United States Patent [19]

Burg

[11] 3,994,423
[45] Nov. 30, 1976

[54] DROP DISPENSING APPARATUS FOR LABORATORY REAGENTS

[75] Inventor: Donald E. Burg, Miami, Fla.

[73] Assignee: American Hospital Supply Corporation, Evanston, Ill.

[22] Filed: Nov. 25, 1974

[21] Appl. No.: 526,957

Related U.S. Application Data

[63] Continuation of Ser. No. 374,763, June 28, 1973.

[52] U.S. Cl. .............................. 222/420; 250/338; 250/573; 73/425.4 P
[51] Int. Cl.² ........................................ B67D 47/18
[58] Field of Search ................... 222/52, 57, 59, 14, 222/76, 399, 420, 422, 70, 421; 250/222 RC, 228, 573, 338, 226; 73/425.4 P

[56] References Cited
UNITED STATES PATENTS

| | | | |
|---|---|---|---|
| 1,993,001 | 3/1935 | Geyer | 73/425.6 |
| 2,784,882 | 3/1957 | DuBois | 222/215 |
| 2,880,764 | 4/1959 | Pelavin | 222/420 X |
| 2,921,715 | 1/1960 | Asset et al. | 222/70 |
| 3,243,595 | 3/1966 | Allington | 250/226 |
| 3,283,727 | 11/1966 | Rodriques, Jr. | 73/425.4 P |
| 3,572,558 | 3/1971 | Hooker | 222/420 |
| 3,771,366 | 11/1973 | Thulin | 73/425.4 P X |

Primary Examiner—Allen N. Knowles
Assistant Examiner—Norman L. Stack, Jr.
Attorney, Agent, or Firm—Tilton, Fallon, Lungmus, Chestnut & Hill

[57] ABSTRACT

An apparatus for the dropwise dispensing of a liquid stored in a reagent bottle or other container, including a tubular probe of inverted J-shaped configuration which communicates with the liquid in the bottle and which is provided with a drop forming and dispensing tip. Gas admitted under pressure to the bottle displaces liquid which passes through the probe until a drop is released at the tip. As the drop falls, it interrupts the light beam of an electro-optic control assembly which in turn actuates a valve to vent the bottle and prevent further liquid discharge from the probe. Because of the configuration and dimensions of the probe, and because of the structural and functional relationship of the probe with other components of the system, the liquid automatically retracts a substantial distance from the probe's free end when such venting occurs, thereby insuring that the tip will remain open and unobstructed for subsequent operation of the apparatus.

6 Claims, 4 Drawing Figures

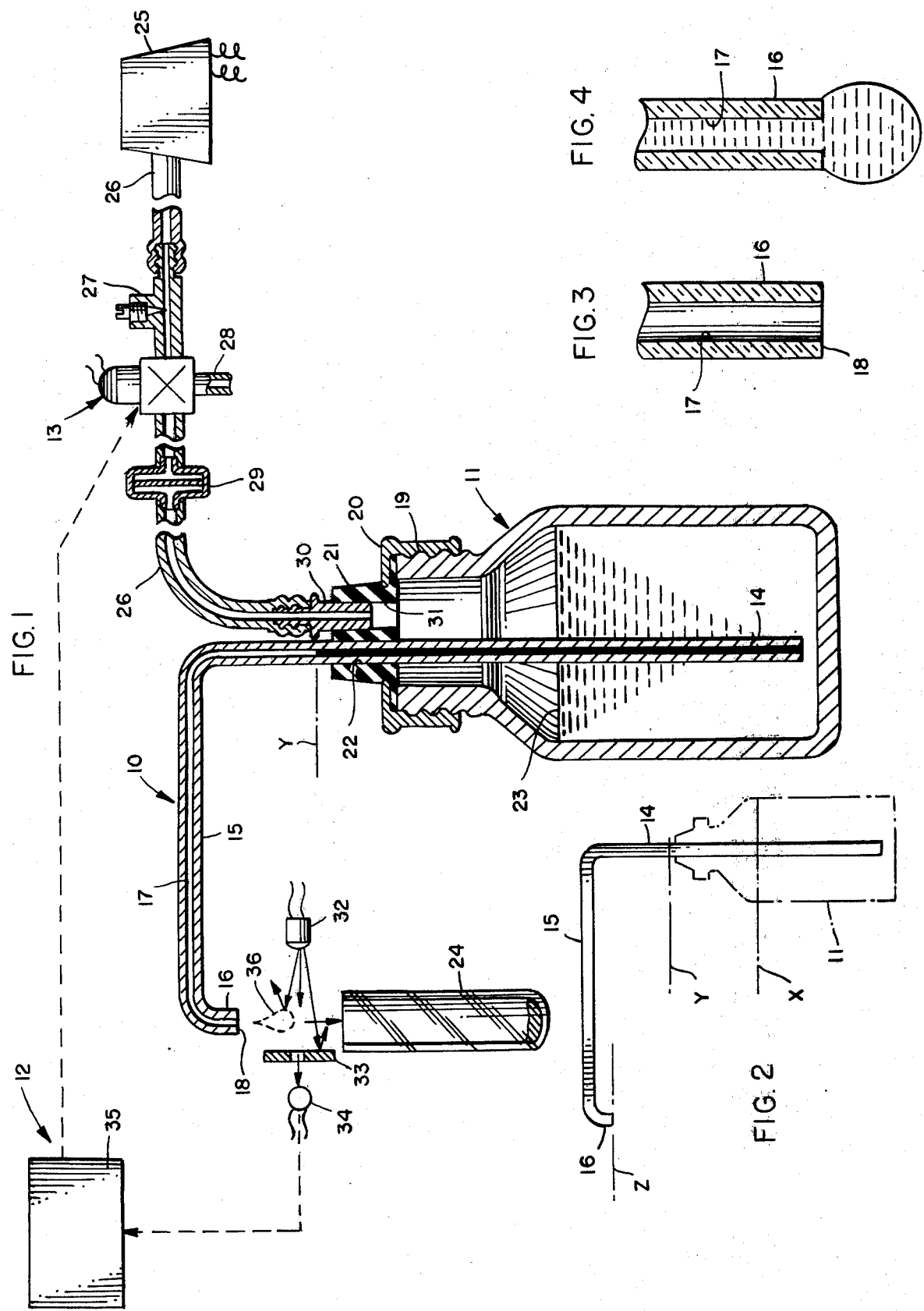

DROP DISPENSING APPARATUS FOR LABORATORY REAGENTS

RELATED APPLICATIONS

This application is a continuation of copending application Ser. No. 374,763, filed June 28, 1973.

BACKGROUND

As is well known, a variety of laboratory test procedures involve the dropwise addition of reagents to institute, maintain, or interrupt the reactions. A typical test, used in the field of immunohematology and blood banking, is the Coombs antihuman globulin test in which one drop (in the indirect Coombs test; two drops in the direct test) of antihuman serum, also known as Coombs serum, prepared from the blood of animals which have been immunized against purified human globulin, is added to a sample of red blood cells to be tested for the purpose of promoting visible agglutination of those erythrocytes which have become coated or sensitized by prior immunologic reaction. If agglutination occurs, it demonstrates the occurrence of a previous reaction between the blood cell antigens and antibody. The test may be used in preparing blood for use in transfusion, with donor's cells and recipient's serum being mixed to ascertain if a combination of antigen and antibody exists, a positive reaction after the addition of antihuman serum indicating incompatibility.

It is believed apparent that a false negative reaction could have serious consequences since it would constitute an incorrect indication of blood compatibility. While automatic analysis equipment is now used with increasing frequency in laboratories because of the greater speed and reliability of automated procedures in contrast to manual procedures, there is a continuing danger that malfunctioning of the equipment might give misleading results. For example, in the operation of equipment designed to carry out the Coombs test, false negative reactions would be expected to occur if for some reason the drop of Coombs serum was not added to each test tube in the final stages of the procedure, or if for some reason an insufficient amount of serum were so added. The problem is further complicated by the fact that upon exposure to air, Coombs serum becomes increasingly viscous and may clog the passage of the drop-dispensing mechanism. While the problem is particularly well illustrated by the Coombs test, and by equipment designed to perform that test automatically, the same problem exists in varying degrees in the automation of other laboratory tests requiring dropwise addition of reagents.

The specific problems described above have not been fully solved in the past despite considerable effort in that regard. Photoelectric devices have previously been known and used for detecting the presence or absence of fluids but such devices, along with other safety measures, have not resulted in automated drop-dispensing laboratory equipment which is sufficiently reliable, non-clogging and substantially maintenance-free. U.S. Pat. Nos. 3,225,191, 3,454,759, 2,446,885, 3,038,300, 3,418,053, 2,718,597, and 3,548,193 are illustrative of the prior art.

SUMMARY

This invention is concerned with a drop-dispensing apparatus for laboratory reagents which is relatively simple in construction and operation and which overcomes the problems described above. The apparatus includes a probe for dispensing drops of liquid such as, for example, antihuman Coombs serum, which is constructed and arranged so that it is non-clogging in operation. Associated with the probe is a photoelectric detector system which detects a drop after it has been released from the probe and is traveling downwardly into the reaction tube, such system cooperating with the drop dispensing portion of the apparatus to trigger the retraction of liquid in the probe immediately after a drop has been released. Because of the substantial extent of liquid retraction in the probe following the dispensing of each drop, the bore of the probe remains clear and unobstructed to insure proper operation when the dispensing of a further drop is later required. Such retraction occurs because of the configuration and dimensions of the probe and because of the structural relationship between the probe and the container and its contents; thus, retraction occurs automatically when the container is vented. Since the venting of the container is caused by deenergization of an electromagnetic valve which is in turn actuated by interruption of a light beam by a falling drop of liquid, liquid in the probe is in its fully retracted condition when the drop dispensing apparatus is in a state of rest.

It is significant that the electro-optic detector is oriented with respect to the probe so that its beam is interrupted only by a drop which is falling from the probe, and not by one which is being formed at the probe's tip. Such a relationship helps to insure that a false signal will not be developed by the drop detector and, in particular, that retraction of liquid in the probe, and other operations of the apparatus which immediately follow drop discharge, will not occur unless a drop has actually been released from the probe and has traveled downwardly along its line of free fall. Reliability and accuracy are further insured by the use of a beam-confining apertured plate and by the fact that the selected photocell, a phototransistor in this case, is sensitive only to light in the infrared portion of the spectrum, to reduce the effects of stray ambient light. It is to be understood, however, that other wavelengths may be used, although such additional advantages will necessarily be sacrificed.

The probe is formed of a relatively rigid and dimensionally stable material, preferably glass, and has an inverted J-shaped configuration. Specifically, the tubular probe includes an elongated depending stem portion which is adapted to extend downwardly into a reagent bottle through a closure extending over the bottle's mouth, an intermediate portion which projects laterally from the stem portion's upper end, and a depending tip portion at the distal end of the intermediate portion. The tip terminates in an annular end surface which extends along a horizontal plane and which has an outside diameter no greater than about 4.0 millimeters. A bore extends throughout the length of the probe and at the probe's tip has a diameter within the range of about 0.25 to 3.0 millimeters. Of particular importance is the fact that the depending tip portion of the probe has a length which constitutes only a minor proportion of the vertical length of the stem portion. The relationship of the probe and bottle is such that the annular end surface of the tip is necessarily disposed a substantial distance above the maximum height to which liquid might rise in the stem by reason of capillary attraction. Therefore, in the absence of positive pressure within the bottle, any liquid in the probe retracts from the tip and intermediate portions into the stem portion.

Other features, advantages, and objects of the invention will become more apparent as the specification proceeds.

DRAWINGS

FIG. 1 is a vertical sectional view of the drop dispensing apparatus with certain components, such as the electro-optic detector system, being illustrated in schematic fashion;

FIG. 2 is a reduced elevational view of the probe and reagent bottle illustrating certain important structural relationships;

FIG. 3 is an enlarged fragmentary vertical sectional view of the tip portion of the probe;

FIG. 4 is an enlarged sectional view similar to FIG. 3 but illustrating the probe tip during drop formation.

DESCRIPTION

The drop dispensing apparatus illustrated in FIG. 1 comprises a probe 10, a reagent container 11, electro-optic drop detector means 12, and gas supply and control means 13. For most applications such gas would be air; however, where necessary or desirable, any other gas or combination of gases might be used.

Probe 10 is formed of a relatively rigid, dimensionally-stable, and non-reactive material such as glass. As shown in FIGS. 1 and 2, the probe is of inverted J-shaped configuration, having an elongated upstanding stem 14, a horizontally-extending intermediate portion 15, and a depending tip 16. The probe is integrally formed as a single tube with a bore 17 extending throughout the full length of that tube. The depending tip 16 terminates in a flat horizontal end surface 18. It has been found that for proper drop formation that annular surface must have a uniform outside diameter no greater than about 4.0 millimeters and an inside diameter within the range of about 0.25 to 3.0 millimeters. For use in a Coombs serum delivery system, the optimum inside diameter is believed to be about 0.5 millimeters.

The container or bottle 11 has an open upper end defined by threaded neck portion 19. Closure means, in the form of cap 20 and resilient stopper 21 seal the mouth of the bottle. As shown most clearly in FIG. 1, the vertical stem 14 extends downwardly through an opening 22 in the stopper, the bottom end of the stem terminating a slight distance above the bottom inside surface of the bottle. The liquid contents of the bottle are designated generally by the numeral 23 with the maximum level of such liquid being represented by line $x$ in FIG. 2. Because of capillary attraction, the level of the liquid within the bore of probe 10 stabilizes at a point well above the level of the liquid in the bottle. The maximum elevation of liquid in stem 14 by reason of such capillary attraction is indicated by line $y$ in FIGS. 1 and 2. That level of liquid within the stem is achieved when the interior of the bottle is at atmospheric pressure and the level of the bottle's fluid contents is at a maximum (i.e., when the bottle is filled to the level represented by line $x$).

It is particularly significant that even when liquid within stem 14 has risen to the maximum level $y$ by reason of capillary attraction, that level is still substantially below the horizontal plane $z$ of the probe's bottom end surface 18. It will also be observed that the difference in elevation between $z$ and $y$ will increase as the contents of the bottle are depleted. Thus, FIGS. 1 and 2 illustrate conditions under which the distance between $y$ and $z$ is at a minimum.

Liquid is discharged from the probe by altering the equilibrium conditions, that is, by increasing pressure within the bottle to displace liquid from the bottle through the probe and into a reaction tube or other receptacle 24. In the illustration given, the pressure increase is achieved by means of the gas supply and control means 13 which includes an air pump 25, conduit 26, needle valve 27, electro-magnetic valve 28, and filter 29. As shown in FIG. 1, conduit 27 is connected to a tubular coupling 30 which is received in passage 31 in stopper 21. Upon operation of the air pump 25, which may be a simple electric diaphragm pump, a stream of air under pressure passes through conduit 26 into the upper end of bottle 11 assuming, of course, that valve 28 is open.

The electro-magnetic control valve 28 is of the type which blocks the flow of air under pressure from pump 25 only when the valve is deenergized. When in a deenergized condition, the electro-magnetic valve vents to atmosphere that portion of conduit 26 extending between valve 28 and bottle 11. Since the construction and operation of such a valve is well known, and since valves of that type are commercially available, a detailed description of the structure and operation of valve 28 is believed unnecessary herein.

The operation of electro-magnetic valve 28 is controlled by the electro-optic drop detector means 12. The latter includes an infrared light source 32, an apertured plate 33 for confining the beam from the source, and an infrared light detector 34. The source of emitter 32 and receiver 34 are part of a circuit 35 which is electrically connected to electro-magnetic valve 28 so that the valve will remain energized, and will therefore admit the flow of pressurized air to bottle 11, as along as the beam of light from source 32 to receiver 34 remains unbroken. Source 32 and receiver 34 are spaced well below the tip or probe 10 with the beam therebetween extending across the path of a drop 36 as it falls directly from the probe's tip towards receptacle 24. Interruption of the infrared beam by the falling drop is detected by receiver 34 and circuit 35 and the latter immediately deenergizes electro-magnetic valve 28, which then remains deenergized until reset by circuit 35 in conjunction with any suitable resetting mechanism (not shown). For example, resetting may be delayed until reaction tube 24 has been withdrawn and another reaction tube has been indexed into position by a suitable transport mechanism (not shown).

While photoelectric detectors are well known, and while elements 32–35 are standard components, the relationship of such elements to the other elements of the apparatus is believed to be unique. Valve 28 is not deenergized until a drop has not only been formed at the end of the probe but has actually been released from the probe and is falling towards the receiving tube 24. The instant the beam is interrupted, air in bottle 11 is vented to the atmosphere and, because of the equalized pressure and the differential head, liquid immediately retracts from the tip and intermediate portions of the probe into stem 14. Because of the retraction of liquid well away from the end surface of tip 16, the dangers that the liquid might become contaminated through exposure at the tip, or might dry or harden and thereby clog the tip, are greatly reduced if not completely eliminated. The result is a relatively simple but highly effective drop dispensing apparatus particularly suitable for use in automated laboratory equipment.

While in the foregoing an embodiment of the invention has been disclosed in considerable detail for purposes of illustration, it will be understood by those skilled in the art that many of these details may be varied without departing from the spirit and scope of the invention.

I claim:

1. A probe for use in the dropwise dispensing of a liquid reagent having a viscosity essentially the same as that of Coombs antihuman serum from a liquid reagent bottle, comprising an inverted J-shaped tube being formed integrally of rigid glass and having a bore of substantially uniform diameter extending throughout its length; said tube having an elongated depending stem adapted to extend downwardly into a reagent supply bottle through the mouth thereof, an intermediate portion projecting laterally from the stem's upper end, and a depending tip at the distal end of said intermediate portion parallel with said stem; said tip terminating in a freely-exposed drop-defining annular end surface extending along a horizontal plane and about a drop discharge opening; said tip having an outside diameter no greater than about 4.0 millimeters; said bore and discharge opening being of a diameter of about 0.5 millimeters; and said tip having a length constituting a minor portion of the length of said stem with said discharge opening being disposed a substantial distance above the maximum height to which liquid might rise in said stem by reason of capillary attraction during operation of said probe.

2. An apparatus for use in the dropwise dispensing of laboratory reagents having viscosity characteristics essentially the same as those of Coombs antihuman serum, comprising a bottle containing a liquid laboratory reagent; said bottle having a mouth at the upper end thereof and having closure means closing said mouth; an inverted J-shaped tube being formed integrally of rigid glass and having a bore of substantially uniform diameter extending throughout its length; said tube having an elongated stem extending downwardly into said bottle through said closure means, an intermediate portion projecting laterally from the stem's upper end, and a depending tip at the distal end of said intermediate portion parallel with said stem; said tip terminating in a freely-exposed drop-defining annular end surface extending along a horizontal plane and about a drop discharge opening; said tip having an outside diameter no greater than about 4.0 millimeters; said bore and said discharge opening being of a diameter of about 0.5 millimeters; and said tip having a length constituting a minor portion of the length of said stem with the end of said tip terminating a substantial distance above the maximum height of said liquid in said bottle and a substantial distance above the maximum height to which liquid in said bottle is capable of rising in said stem by reason of capillary attraction.

3. The structure of claim 2 in which said closure means is provided with a passage for the selective introduction of gas under pressure into said bottle and the resulting displacement of liquid from said bottle through said tube.

4. An apparatus for the dropwise dispensing of laboratory reagents having viscosity characteristics essentially the same as those of Coombs antihuman serum, comprising a bottle containing a liquid laboratory reagent; said bottle having a mouth at the upper end thereof and having closure means closing said mouth; an inverted J-shaped tube having an elongated stem extending downwardly into said bottle through said closure means, an intermediate portion projecting laterally from the stem's upper end, and a depending tip at the distal end of said intermediate portion; said tip terminating in an annular end surface extendin g along a generally horizontal plane; said tube having a bore extending therethrough of a diameter of about 0.5 millimeters; said tip having a length constituting a minor portion of the length of said stem with said annular end surface disposed a substantial distance above the maximum height to which liquid in said bottle is capable of rising into said stem by reason of capillary attraction; said closure means being provided with a passage for the selective introduction of gas under pressure into said bottle for the displacement of liquid from said bottle through said tube; means communicating with said passage for selectively discharging gas under pressure into said passage; valve means interposed along said passage for interrupting the flow of gas under pressure into said bottle and for simultaneously venting said passage and bottle to atmospheric pressure, whereby, upon the interruption of said gas flow and the venting of said passage and bottle to atmospheric pressure, liquid in said tube retracts from said tip and intermediate portion into said stem.

5. The structure of claim 4 in which detector means are disposed below said tip for detecting the release of a drop of liquid from said tip and for actuating said valve means to interrupt said gas flow and cause retraction of said liquid in said tube when said detection occurs.

6. The structure of claim 5 in which said detector means includes an infrared light source and an infrared light receiver disposed on opposite sides of the path of travel of a drop falling from the tip of said tube.

* * * * *